United States Patent
Costa De Beauregard et al.

[11] Patent Number: 5,888,722
[45] Date of Patent: Mar. 30, 1999

[54] STABLE CELL LINES EXPRESSING THE CFTR PROTEIN OR A MUTANT OF THIS PROTEIN, TOOL FOR SELECTING MOLECULES HAVING AN EFFECT ON THE INTRACELLULAR TRANSPORT OF THESE PROTEINS

[75] Inventors: Marie-Alyette Costa De Beauregard; Daniel Louvard; Sylvie Robine; Alexandre Edelman, all of Paris Cedex; Dominique Chesnoy-Marchais, Paris, all of France; Ming Chen; Manuel Buchwald, both of Toronto, Canada

[73] Assignees: Institut Curie; Centre National de la Recherche Scientifique, both of Paris, France

[21] Appl. No.: 874,040

[22] Filed: Jun. 12, 1997

[30] Foreign Application Priority Data

Nov. 4, 1996 [FR] France .................................. 96 13416

[51] Int. Cl.$^6$ .............................. C12Q 1/00; C12P 21/06; C12N 15/00; C07H 17/00
[52] U.S. Cl. .......................... 435/4; 435/320.1; 435/325; 435/69.1; 536/23.1; 536/24.1
[58] Field of Search .......................... 435/4, 69.1, 320.1, 435/325; 536/23.1, 24.1

[56] References Cited

FOREIGN PATENT DOCUMENTS

WO 94/04671  3/1994  WIPO .
WO 95/05810  3/1995  WIPO .

OTHER PUBLICATIONS

Costa de Beauregard, "Establishment of Kidney Epithelial Cell Lines Expressing Wild Type and CFTR (ΔF508) With an Epitope Tag in View of Functional Studies on CFTr (ΔF508) Trafficking", ICF(M)A (1996).

Bergeron et al, "Calnexin: a membrane–bound chaperone of the endoplasmic reticulum", TIBS 19(3):124–128 (1994).

Yang et al, "The common variant of cystic fibrosis transmembrane conductance regulator is recognized by hsp70 and degraded in a pre–Golgi nonlysosomal compartment", Proc. Natl. Acad. Sci. USA 90:9480–9484 (1993).

Pind et al, "Participation of the Endoplasmic Reticulum Chaperone Calnexin (p88, IP90) in the Biogenesis of the Cystic Fibrosis Transmembrane Conductance Regulator", Journal of Biological Chemistry 269(17):12784–12788 (1984).

Robine et al, "Regulatory Sequences on the Human Villin Gene Trigger the Expression of a Reporter Gene in a Differentiating HT29 Intestinal Cell Line", Journal of Biological Chemistry 268(15):11426–11434 (1993).

Hammond et al, "Role of N–linked oligosaccharide recognition, glucose trimming, and calnexin in glycoprotein folding and quality control", Proc. Natl. Acad. Sci. USA 91:913–917 (1994).

Hammond et al, "Folding of VSV G Protein: Sequential Interaction with BiP and Calnexin", Science 266:456–458 (1994).

Jackson et al, "Regulation of MHC Class I Transport by the Molecular Chaperone, Calnexin (p. 88, IP90)", Science 263–384–390 (1994).

Rajagopalan et al, "Retention of Unassembled Components of Integral Membrane Proteins by Calnexin", Science 263:387–390 (1994).

Kreis, "Microinjected antibodies against the cytoplasmic domain of vesicular stomatitis virus glycoprotein block its transport to the cell surface", The EMBO Journal 5(5):931–941 (1986).

*Primary Examiner*—Karen Cochrane Carlson
*Attorney, Agent, or Firm*—Nixon & Vanderhye P.C.

[57] ABSTRACT

The invention relates to a recombinant nucleic acid, characterized in that it comprises:

- a nucleotide sequence encoding (coding sequence) the normal CFTR protein,
- an epitope sequence located at the 3' end of the abovementioned coding sequence,
- a strong promoter sequence capable of controlling the expression of the abovementioned coding sequence and epitope sequence, when they are integrated into a determined cell.

20 Claims, 3 Drawing Sheets

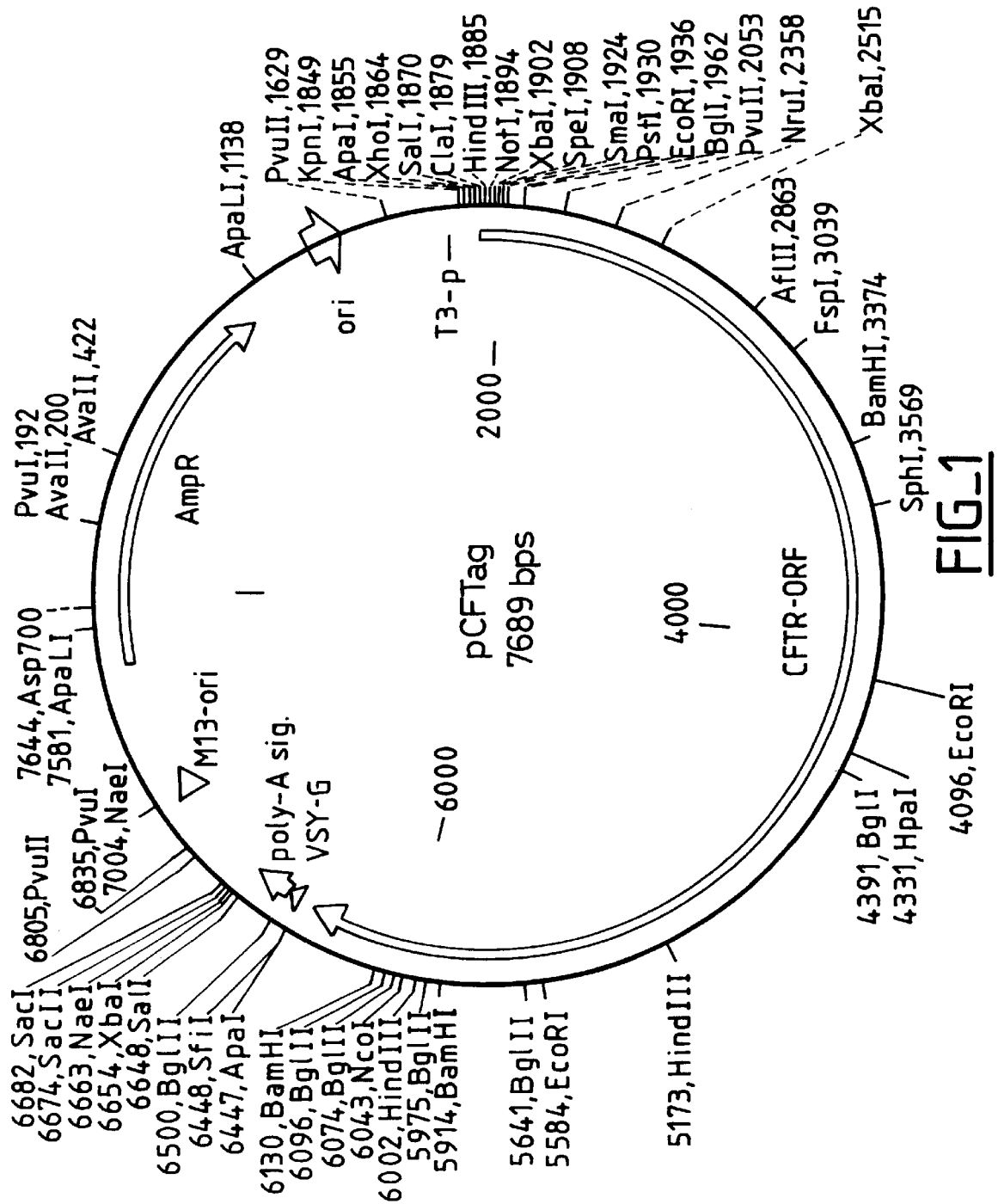

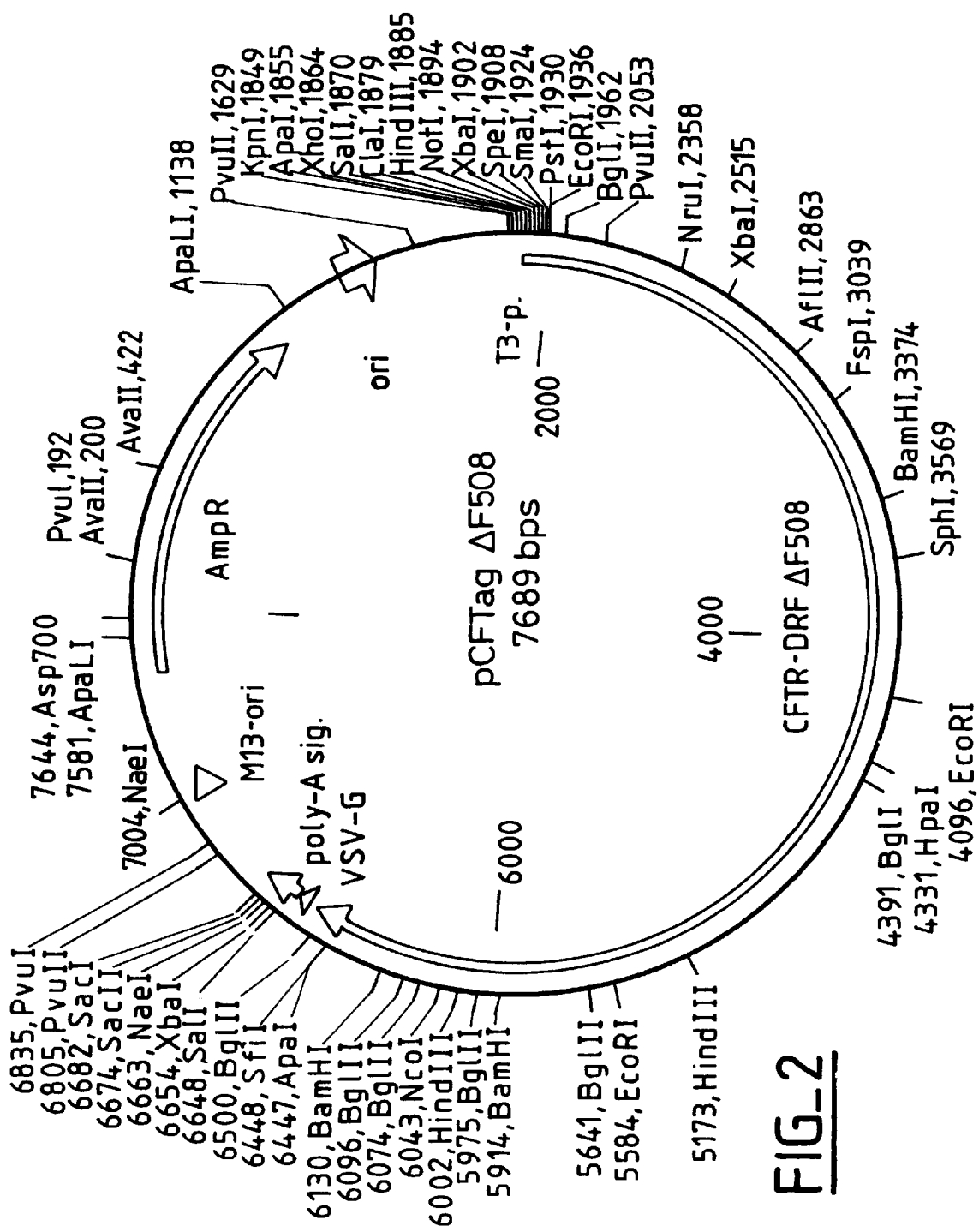
FIG_2

USE OF THE TERMINAL NUCLEOTIDE SEQUENCE OF VSV-G (VESICULAR STOMATITIS VIRUS-GLYCOPROTEIN)

Kreis, 1986; EMBO J., 5, 931-941

NUCLEOTIDE SEQUENCE:

Smal  Apal

CCGGGAGGGCCCACCAGGCCCA TACACCGACACATCGAGATGAACCGGCTGGGCAAG TAA AGATCTAAGGTACCAATCTAGACTAG

Site Sfi I     Sequence of VSV-G     Stop Sites Bgl II    Kpn I    Xba I (3' end)

PRIMARY SEQUENCE:

G P P G P     Y T D I E M N R L G K

Spacer     Tag

Recognition by monoclonal antibody $P_5 D_4$

FIG_3

STABLE CELL LINES EXPRESSING THE CFTR PROTEIN OR A MUTANT OF THIS PROTEIN, TOOL FOR SELECTING MOLECULES HAVING AN EFFECT ON THE INTRACELLULAR TRANSPORT OF THESE PROTEINS

The subject of the invention is stable cell lines expressing the CFTR (Cystic Fibrosis Transmembrane Conductant Regulator) protein, as well as mutants of this protein. The application also relates to the use of these lines as screening tools for determining the effect of selected molecules on the intracellular transport of these proteins.

Cystic fibrosis (CF) is a recessive autosomal genetic disease which is frequent within certain populations and which is specifically characterized by a functional impairment of the exocrine glands of the human organism, resulting from mutations of the cftr gene which leads to modifications of the function of the CFTR-chlorine channel.

The cftr gene has been cloned and sequenced and its characterization has been reported in the following publications: Kerem B. S., et al., Science 1989, 245: 1073–80; Riordan J. R., et al., Science, 1989, 245: 1066–73 and Rommens J. M. et al., Science 1989, 245: 1059–64. On this occasion, the complementary DNA sequence (cDNA) was identified and described (Riordan J. R. et al., cited above).

Cystic fibrosis is manifested by an overall insufficiency of the exocrine secretions, especially at the level of the pancreas and the lungs and clinically corresponds to the observation of excessively viscous secretions, the disorders resulting therefrom being capable of leading to the death of the patient.

Following the demonstration of the role of the gene encoding the CFTR protein in the development of the disease, various pathways have been the subject of research studies in order to provide therapeutic means for treating the affected patients.

Among the mutations of the cftr gene observed in patients, one of them is manifested by the expression of a mutated CFTR protein called CFTR($\Delta$F508). This mutation of the gene is manifested by the deletion of the phenylalanine residue at position 508 of the CFTR protein. It is the most frequent of the 400 mutations observed up until now at the level of the cftr gene, since it represents 70% of the mutations observed in patients.

This mutation affects the maturation and the intracellular transport of the CFTR($\Delta$F508) protein.

Within the framework of the present patent application, the inventors focused on means which can be used for screening known or new molecules in order to identify among them agents which may be involved in the restoration of the intracellular transit of the mutated CFTR protein present in patients suffering from cystic fibrosis.

In this regard, the inventors observed in particular the behaviour of the mutated CFTR protein ($\Delta$F508), it being understood, however, that the teaching resulting from the observations made is equally applicable within the framework of the invention to other mutated CFTR proteins, whose phenotype is analogous to that of the CFTR($\Delta$F508) protein, corresponding to a phenotype for retention in the endoplasmic reticulum.

The subject of the invention is nucleic acid constructs, and in particular DNA or cDNA comprising a nucleotide sequence encoding the normal CFTR protein or a nucleotide sequence encoding a mutated variant and especially the CFTR($\Delta$F508) protein.

The subject of the invention is also transformed cells and stable recombinant cell lines comprising these constructs.

A first construct which can be used to express, under controlled conditions, the CFTR protein or a mutant of this protein, in particular a mutant ($\Delta$F508), is a recombinant nucleic acid comprising:

a nucleotide sequence encoding (coding sequence) the normal CFTR protein, an epitope sequence located at the 3' end of the abovementioned coding sequence and, a strong promoter sequence capable of controlling the expression of the abovementioned coding sequence and epitope sequence when they are integrated in to a determined cell.

The coding sequence described above is advantageously a cDNA sequence which can be derived from the cftr gene. This cDNA sequence has been published (Riordan J. R. et al., cited above) and may be obtained by any means known per se.

Alternatively, the coding nucleotide sequence defined above, which is capable of expressing the normal CFTR protein, is replaced by a nucleotide sequence encoding the mutated CFTR protein ($\Delta$F508) (mutated coding sequence). This sequence is preferably a cDNA sequence.

A selectable marker, in particular a gene for resistance to an antibiotic, for example a gene for resistance to neomycin, may be advantageously added to the recombinant nucleic acid construct.

The epitope sequence or "tag" used within the context of the construct described above is chosen so as to be specifically recognized by a monoclonal antibody of high affinity. This epitope sequence is located in the recombinant nucleic acid, so as not to impair the functionality of the normal or mutated CFTR protein expressed, when the recombinant nucleic acid is placed in a determined cell. According to a specific embodiment of the invention, the epitope sequence is added to the 3' end of the sequence encoding the normal or mutated CFTR protein.

Advantageously, use will be made of an epitope sequence such as the sequence encoding the G protein of the vesicular stomatitis virus (VSV) (Kreis T. E., EMBO J., 1986, 5, 931–941).

The promoter used in the recombinant nucleic acid construct is advantageously a strong promoter and, for example, a viral promoter, especially the cytomegalovirus (CMV) promoter. This may also be other viral promoters or promoters specific for a given tissue such as the human villin promoter (Robine et al., J. Biol. Chem., 1993, 268, 11426–11434).

The subject of the invention is also a recombinant cloning and expression vector comprising a recombinant nucleic acid as defined above. This vector may be a plasmid and especially the plasmid pCFTag or the plasmid pCFTag$\Delta$F508. It may also be a viral vector.

The subject of the invention is also recombinant cells, especially eukaryotic cells, chosen from polarized cells not endogenously expressing the cftr gene, the said cells containing, in addition, a recombinant nucleic acid according to the invention or a vector as defined above.

These cells are transformed by any cell transforming technique known per se and may be transfected in particular, for example, by lipofection.

Preferably, the recombinant cells are cells derived from epithelial cells.

A particularly advantageous cell line within the context of carrying out the invention is the stable and homogenous cell line LLC.$\Delta$6.5 deposited at the Collection Nationale de Cultures de Microorganismes in Paris (C.N.C.M.) (Institut Pasteur, 25, rue Du Docteur Roux, 75724 Paris, CEDEX, 15, France) under the No. I-1779 on 4 Nov. 1996. This cell line is capable of expressing a recombinant nucleic acid according to the invention in the form of a mutated CFTR protein (ΔF508).

Another cell line which can be used especially as control is the line LLC.CFt6.1 deposited at the CNCM under the No. I-1780 on 4 Nov. 1996, which is capable of expressing the normal CFTR protein.

According to a variant embodiment of the invention, the cell lines are obtained by transforming the chosen cells with a recombinant nucleic acid according to the invention, the latter being, however, free of the epitope sequence termed "tag".

The epithelial cell line LLC.Δ6.5 can be used in the framework of the invention as a means for testing for pharmacologically active agents capable of restoring the intracellular transport of the mutated CFTR protein ΔF508 to the apical membrane of the cells. The LLC.CFt6.1 line may be used as control in the context of such a screening process.

To do this, use will be made of a process for determining the effect of a given molecule on the transport of the mutated CFTR protein (ΔF508) to the membrane of cells expressing it, comprising:
  bringing a chosen molecule into contact with the LLC.Δ6.5 cell line (CNCM No. I-1779) under conditions allowing interaction between the molecule tested and the proteins expressed by the cell,
  detecting the presence of the mutated CFTR protein (ΔF508) at the apical cell membrane of the cells of the LLCPK1 line.

The carrying out of this process may make it possible to study the modifications of the interaction between the mutated CFTR protein and a chaperone molecule such as calnexin, which prevents the transport of this mutated CFTR protein to the apical membrane of the cells.

In particular, molecules capable of interaction with the retaining function exerted by the chaperone protein, in particular calnexin, on the proteins expressed and retained in the endoplasmic reticulum of the cells, will be selected in this context.

Within the framework of the present invention, a protein derived from calnexin is also used, in which the retention signal has been deleted or made non-functional. The inventors also showed that the protein thus truncated is no longer capable of retaining at the level of the endoplasmic reticulum proteins which would be by the normal calnexin, in particular the CFTR(ΔF508) protein.

The subject of the present application is also a cell line derived from the recombinant cells defined above, the said line expressing, in addition, a protein derived from a chaperone protein, in particular calnexin, whose signal for retention in the endoplasmic reticulum has been truncated. These lines may be obtained by transforming the LLCPK1, LLC.Δ6.5 or LLC.CFt6.1 lines with the aid of cDNA encoding the mutated calnexin. In this regard, the publication by Rajagopalan S. et al. (Science, 1994, 263, 387–390) describes appropriate plasmid constructs.

Preferably, the truncated calnexin is overexpressed compared with the endogenous normal calnexin. A line thus established constitutes a means for studying the restoration of the transport of the mutated CFTR protein (ΔF508) to the cell membrane.

The invention also relates to the LLC.Δ6.5 or LLC.CFt6.1 cell lines transformed with a DNA sequence encoding the normal calnexin. To do this, the cDNA sequence of human calnexin is used in particular, for example, in the constructs described by Rajagopalan et al.

The subject of the present application is therefore also a process for determining the effect of a given molecule on the interaction between calnexin and the mutated CFTR protein (ΔF508), comprising:
  bringing a chosen protein into contact with an LLC.Δ6.5 cell line expressing the calnexin protein,
  detecting the presence of the mutated CFTR protein (ΔF508), at the apical cell membrane of the cells of the line.

Alternatively, the subject of the invention is a process for detecting the effect of a chosen molecule on the interaction between human calnexin, preferably obtained in recombinant form, and the mutated CFTR protein (ΔF508), the said process consisting in:
  placing calnexin and the CFTR(ΔF508) protein under conditions for interaction,
  bringing the abovementioned proteins into contact with a chosen molecule capable of reacting with these proteins and, in particular, capable of modifying the interaction between calnexin and the CFTR(ΔF508) protein,
  observing, where appropriate measuring the interaction between calnexin and the CFTR(ΔF508) protein.

Tests which can be used in this regard comprise the techniques used in the Biacor test (Pharmacia), the technique for producing a double hybrid, or the "phage display" technique.

Other properties characteristic of the invention will appear in the examples and the figures which follow.

FIG. 1: restriction map of the plasmid pCFTag comprising the cDNA encoding the CFTR protein, the epitope sequence of the G protein of the VSV virus, under the control of the CMV promoter, the gene for resistance to ampicillin and the marker gene for resistance to neomycin.

FIG. 2: restriction map of the plasmid pCFTagΔF508 comprising the cDNA encoding the CFTR(ΔF508) protein, the epitope sequence of the G protein of the VSV virus, under the control of the CMV promoter, the gene for resistance to ampicillin and the marker gene for resistance to neomycin.

FIG. 3: use of the terminal nucleotide sequence of VSV-G in the constructs (SEQ ID NO:1 and SEQ ID NO:2).

Development of Immunological and Pharmacological Tools for Studying the Expression and Intracellular Transport of the Normal or Mutated (ΔF508) CFTR Protein The study ex vivo and in vivo of the expression and addressing of the normal or mutated (ΔF508) CFTR protein was up until now limited because of the low specificity of the existing antibodies. With the aim of developing an immunological tool for this type of study, the inventors used cDNAs coding for the normal CFTR protein (Riordan J. R. et al., Science 1989, 245: 1066–1080) or for the mutated protein ΔF508 (Morgenstern J. P. et al., Nucleic Acids Rs., 1990, 18: 3587–3596). These cDNAs were genetically modified by the addition of an epitope sequence consisting of the G protein of the vesicular stomatitis virus (Kreis T. E., EMBO J., 1986, 5: 931–941), in 3' of the cDNA sequences. This epitope sequence (tag) encodes an antigen specifically recognized by a monoclonal antibody P5D4 of high affinity (Kreis T. E., EMBO J., 1986, 5: 931–941). Stable clones of differentiated epithelial cells LLCPK1 (ATCC No. CL1) transfected with these constructs under the control of the strong cytomegalovirus (CMV) viral promoter were obtained. The cell lines expressing the marked CFTR (ΔF508) protein are used to test for pharmacological agents capable of restoring the apical transport of CFTR(ΔF508).

A. Materials and Methods

1. Construction of the Plasmids pCMV/CFtag

The cDNA of the normal cftr gene was inserted into the vector pCB6 (Algrain M. et al., J. Cell. Biol., 1993, 120, 129–139) downstream of the cytomegalovirus (CMV) promoter. This vector comprises a gene for resistance to ampicillin, and the gene for resistance to neomycin which serves as selectable marker. The sequence encoding the protein G antigen of the vesicular stomatitis virus (tag) was inserted in phase with the open reading frame of the cDNA of the cftr gene, at its 3' end.

pCMV/CF(ΔF508) tag

This plasmid was constructed according to the same principle as the vector pCMV/CFtag. The only difference is that the cDNA inserted downstream of the strong CMV viral promoter is that encoding CFTR(ΔF508).

Aprm8.2kb

The cDNA encoding normal human calnexin was inserted into the vector Aprm8 (Rajagopalan S. et al., Science, 1994, 263, 387–390) downstream of the cytomegalovirus (CMV) promoter. The vector Aprm8 comprises the gene for resistance to ampicillin. The 2 kb fragment encoding human calnexin was cut at each end with the restriction enzyme SpcI, and inserted into the HbaI site of the polylinker of the vector Aprm8.

Aprm8.CT

This plasmid was constructed according to the same principle as the vector Aprm8.2kb. The only difference was that the cDNA inserted downstream of the strong CMV viral promoter is that encoding human calnexin whose cytoplasmic tail has been deleted. This cDNA was obtained by PCR and then cut at each end with the restriction enzyme EcoRI, and inserted into the EcoRI site of the polylinker of the vector Aprm8.

2. Cell Culture

The line of epithelial cells LLCPK1 derived from pig kidney tubules is cultured in DMEM (Dulbecco's minimum essential medium) medium supplemented with: 10% foetal calf serum (Biological Industries, tested for mycoplasma and virus, batch No. 085712), glucose 25 mM and L-glutamine 2 mM. They are kept at 37° C., in a humid atmosphere in the presence of 10% $CO_2$ (Pinto et al., 1982–1983).

3. Transfections of the LLCPK1 Cells

The cells were transfected with lipofectin (BRL) which induces the formation of lipid-DNA complexes (Feigner et al., 1987). The transfection is carried out on cells in the exponential growth phase which have been subcultured the day before at a density of about $10^5$ cells per culture dish 3 cm in diameter. The culture medium was changed 2 h before transfection. The cells were washed twice with FCS-free DMEM culture medium. The lipofectin was heated for 2 min at 40° C. and then incubated with the plasmids (10 μl of lipofectin per 5 μg of plasmid) in sterile water for 15 min at room temperature. The micelles thus formed were diluted in FCS-free DMEM medium and exposed to the cells which were maintained at 37° C. Control cells were incubated with the same quantity of lipofectin micelles without plasmid. The standard culture medium was re-established 6 h later.

4. Establishment of Stable Lines of LLCPK1 Cells

After transfection with the plasmids pCMV/CFtag or pCMV/CF(ΔF508)tag, the cell culture was continued to preconfluence, and then subcultured at low density. G418 (Gibco BRL) was then added at the concentration of 2 mg/ml. This minimum lethal concentration was established beforehand by culturing non-transfected cells in the presence of increasing concentrations of G418. The resistant clones were isolated by trypsinisation by means of rings, and then each separately cultured, the selection pressure being maintained by the G418 at 1 mg/ml.

A clone established after transfection with the plasmid pCMV/CF(ΔF508)tag was co-transfected with the plasmid PHA58, containing the gene for resistance to hygromycin, and the plasmid Aprm8.2kb or Aprm8.CT according to the conditions described above. Stable lines were established; the selection of the resistant clones was obtained in cell culture medium containing 2 mg/ml of G418, and 0.4 mg/ml of hygromycin B (Boehringer Mannheim).

5. Test Using the Fluorophore 6-methoxy-N-3-sulphopropyl Quinolinium (SPQ)

The anion channel function of the tagged CFTR protein was evaluated by a test based on the measurement of the intensity of fluorescence of the SPQ compound sensitive to the anion concentration of the medium (D. Rich et al., Nature 347: 358–363; 1990, Rommens et al., Proc. Acad. Sci. USA 88: 7500–7504; 1991).

The experimental procedure is as follows:

The fluorophore 6-methoxy-N-3-sulphopropyl quinolinium (SPQ) is loaded into the cells by a hypo-osmotic shock. After a short period for the cells to recover, the base anion conductance is measured by exposing the cells to an iodinated solution, and then to an $NO_3$ solution, and then again to an iodinated solution. Iodine is used rather than chorine in the SPQ test because the fluorescence extinction is more sensitive to the addition of iodine than to that of chlorine (Ilsley and Verkman Biochemistry 26: 1215–1219, 1987). All the solutions were supplemented with 10 μM bumetanide which is an inhibitor of Na/K/Cl co-transporter.

The anion channel activity of CFTR was tested by the addition to the solution of $NO_3$, 500 μM CPT-cAMP, 10 μM forskolin and 100 μM IBMX (isobutyl-methyl-xanthine).

B. Establishment of Stable Cell Clones Expressing the Tagged Normal or Mutated CFTR Protein The LLCPK1 cells (ATCC No. Cl 101), derived from pig kidney proximal tubule, have no activity linked to a cAMP-dependent chlorine channel. It is one of the reasons for their choice for the establishment of stable clones expressing the tagged CFTR protein. The constructs were prepared with the cDNA encoding the normal CFTR or mutated CFTR (ΔF508) protein, placed under the control of the strong CMV viral promoter. The plasmids used contain the gene for resistance to neomycin, used as selectable marker. The cells were transfected by lipofection. After 3 weeks of selection in the presence of G418, the clones were isolated by the cloning ring technique.

2 clones transfected with the plasmid comprising the wild-type cDNA, and 3 clones transfected with the plasmid comprising the cDNA (ΔF508), exhibiting 30 to 40% of positive cells in immunoprecipitation of the protein with the aid of the P5D4 antibody. The functionality of CFTR is studied by tests using the fluorophore SPQ, which is sensitive to the chlorine flows (Rich D. P. et al., Nature, 347: 358–363, 1990 and Rommens J. M. et al., Proc. Acad. Sci. USA, 88: 7500–7504, 1991).

The intracellular distribution of CFTR is that expected; the protein is located at the apical membrane in the clones transfected with the wild-type form. The mutated form (ΔF508) is expressed in the endoplasmic reticulum where it is collocated with calnexin.

This suggests that the chaperone protein calnexin interacts with the CFTR(ΔF508) protein at the level of the endoplasmic reticulum. This interaction involves immature N-glycosylated chains of the CFTR protein and would be responsible for the retention of the CFTR(ΔF508) protein in the endoplasmic reticulum.

B. Test for Pharmacological Agents Capable of Restoring the Apical Transport of the CFTR(ΔF508) Protein The ΔF508 mutation of the cftr gene is by far the most frequent in patients suffering from cystic fibrosis since it represents about 68% of the mutations recorded. The mutated protein is retained in the endoplasmic reticulum (ER), which prevents its maturation, in particular the addition of certain sugars, its addressing to the apical membrane (review in Ferec et al., Médecine/Sciences, 1994, 10, 631–639). The functionality of the CFTR(ΔF508) protein (chlorine channel regulated by phosphorylation) has been demonstrated (Li et al., Nat. Genet., 1993, 3, 311–316). It has also been shown that after two days of incubation at 23° C., the mutated protein is partly located at the apical pole (Denning al., Nature, 1992, 358, 761–764). However, such conditions cannot be envisaged in clinical therapy; it therefore appears important to characterize pharmacological agents capable of correcting or restoring the transport of the CFTR(ΔF508) protein from the endoplasmic reticulum to the cell surface. Such molecules would be an alternative to gene therapy if they prove applicable in clinical medicine.

It has been shown that the chaperone proteins, in particular calnexin, interact with the incompletely glycosylated CFTR(ΔF508) protein (Yang et al., Proc. Natl. Acad. Sci. USA, 1993, 90, 9480–9484) and might be partly or completely responsible for its retention at the level of the ER (review in Puchelle, Médecine/Sciences, 1994, 10, 627–629). Calnexin is a chaperone protein which is involved in the protein folding during maturation in the ER. It has been shown that it is co-immunoprecipitated with the immature CFTR protein (Pind et al., J. Biol. Chem. 1994, 269, 12784–12788).

Two different strategies for trying to displace the calnexin/CFTR(ΔF508) protein interaction have been envisaged.

1. Use of Oligosaccharides which are Competitors for the Calnexin/immature CFTR Protein Interaction The interaction of calnexin with certain newly synthesized proteins such as the influenza virus hemaglutinin and the vesicular stomatitis virus G protein is prevented by the inhibitors of N-glycosylations (tunicamycin) and of glycosidases I and II (catanospermine and 1-deoxynojirimycin) (Hammond et al., 1994). This shows the role of N-glycosylations in the calnexin/newly synthesized protein interactions. Such molecules being unusable in therapy because of their toxicity, it appeared useful to try to prevent the interaction between the two proteins by displacing the N-glycosylated chains of the CFTR(ΔF508) glycoprotein from the site of interaction with calnexin by entering into competition with a synthetic carbohydrate. The glycoside sequence which interacts with calnexin is indeed a glucose directly linked to a mannose.

2. Use of a "Dominant-negative" Modified Calnexin

Calnexin is a transmembrane protein located in the ER. It has a short cytoplasmic domain and a large intraluminal domain through which it interacts with the immature proteins in the course of glycosylation. The overexpression of a mutated form of calnexin at the level of the signal for retention in the ER could allow the mutated CFTR protein to be addressed to the plasma membrane. This mutated form of calnexin, by interacting with the immature protein, would allow addressing, to the plasma membrane, of the complex formed between the mutated calnexin and the complex mutated CFTR protein which would therefore not be retained at the level of the ER. When it is overexpressed, this mutated calnexin protein therefore acts as a dominant negative by displacing the interaction of the endogenous calnexin with the immature CFTR protein. The effect of this "dominant negative" on the addressing of the tagged CFTR (ΔF508) protein in the LLCPK1 cell clones obtained is under evaluation. Experiments of transient transfections of mutated calnexin are carried out, and double transfectant (for CFTR(ΔF508) and for mutated calnexin) stable lines are selected. For that, a second selectable marker (Hygromycin R) is used.

According to this experimental protocol, LLCPK1 clones doubly transfected with the CFTR(ΔF508) and the truncated human calnexin constructs have been obtained, as well as clones transfected with the CFTR(ΔF508) and the entire human calnexin constructs.

In clones expressing CFTR(ΔF508) and the truncated human calnexin, the cellular localization of CFTR(ΔF508) is modified. By indirect immunofluorescence, CFTR(ΔF508) is observed in large intracellular vesicles different from the endoplasmic reticulum where CFTR(ΔF508) is normally retained.

In the clones expressing CFTR(ΔF508) and the entire human calnexin, the cellular localization of CFTR(ΔF508) is not modified.

These observations demonstrate that the overexpression of a truncated form of calnexin promote the release of a significant fraction of the CFTR(ΔF508) from the endoplasmic reticulum (dominant effect: gain of function). These data demonstrate that calnexin is a major molecular determinant in the retention of CFTR(ΔF508) in the endoplasmic reticulum.

We claim:

1. An isolated nucleic acid molecule comprising:
   i) a nucleotide sequence encoding normal cystic fibrosis transmembrane conductance regulatory (CFTR) protein,
   ii) a nucleotide sequence encoding an epitope added to the 3' end of the nucleotide sequence encoding normal CFTR protein, and
   iii) a nucleotide sequence encoding a strong promoter,
   wherein said nucleotide sequence encoding said strong promoter is operatively linked to the nucleotide sequence encoding normal CFTR protein.

2. An isolated nucleic acid molecule comprising:
   i) a nucleotide sequence encoding cystic fibrosis transmembrane conductance regulator (CFTR) protein being mutated such that the mutated CFTR protein is retained in an endoplasmic reticulum,
   ii) a nucleotide sequence encoding an epitope added to the 3' end of the nucleotide sequence encoding said mutated CFTR protein, and
   iii) a nucleotide sequence encoding a strong promoter,
   wherein said nucleotide sequence encoding said strong promoter is operatively linked to the nucleotide sequence encoding said mutated CFTR protein.

3. The nucleic acid molecule of claim 1, said nucleic acid molecule further comprising a selectable marker.

4. The nucleic acid molecule of claim 2, said nucleic acid molecule further comprising a selectable marker.

5. The nucleic acid molecule of claim 1 or claim 2, wherein the expressed epitope is specifically recognized by a monoclonal antibody.

6. The nucleic acid molecule of claim 1 or claim 2, wherein the nucleic acid sequence encoding an epitope encodes the G protein of the vesicular stomatitis virus.

7. The nucleic acid molecule of claim 1 or claim 2, wherein the promoter is a viral promoter.

8. The nucleic acid molecule of claim 7, wherein the viral promoter is the cytomegalovirus promoter.

9. The nucleic acid molecule of claim 1 or claim 2, wherein the promoter is a tissue-specific promoter.

10. The nucleic acid molecule of claim 9, wherein the tissue-specific promoter is the human villin promoter.

11. An expression vector comprising the nucleic acid molecule of anyone of claims 1 or 2.

12. An isolated eukaryotic host cell comprising the nucleic acid molecule of claim 1.

13. An isolated eukaryotic host cell comprising the nucleic acid molecule of claim 2.

14. An isolated eukaryotic host cell comprising the nucleic acid molecule of claim 3.

15. The host cell of claim 12 or claim 13, wherein said host cell is an epithelial cell.

16. The host cell of claim 12 or 13, wherein the host cell further expresses a truncated calnexin protein lacking its retention signal.

17. Cell line LLC.CFt6.1 (CNCM I-1780).

18. Cell line LLC.Δ6.5 cell line (CNCM No. I-1779).

19. A method for determining the effect of a given molecule on the transport of the mutated CFTR protein ΔF508 to the membrane of the cells expressing it, comprising:
   bringing a chosen molecule into contact with the LLC.Δ6.5 cell line (CNCM No. I-1779) under appropriate conditions for interaction,
   detecting the presence of the mutated CFTR protein ΔF508 at the apical cell membrane of the cells of the LLC.Δ6.5 line.

20. A method for determining the effect of a given molecule on the interaction between calnexin and the mutated CFTR protein ΔF508, comprising:
   bringing a chosen molecule into contact with the LLCΔ6.5 cell line (CNCM No. I-1779),
   detecting the presence of the mutated CFTR protein ΔF508, at the apical cell membrane of the cells of the line.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 84 base pairs
        ( B ) TYPE: nucleic acid
        ( C ) STRANDEDNESS: double
        ( D ) TOPOLOGY: linear ( i i ) MOLECULE TYPE: DNA (genomic)

-continued ( x i ) SEQUENCE DESCRIPTION: SEQ ID NO: 1:

CCGGGAGGGC CCACCAGGCC CATACACCGA CATCGAGATG AACCGGCTGG GCAAGTAAAG 60

ATCTAAGGTA CCAATCTAGA CTAG 84

( 2 ) INFORMATION FOR SEQ ID NO: 2:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 2:

Gly Pro Pro Gly Pro Tyr Thr Asp Ile Glu Met Asn Arg Leu Gly Lys
1               5                   10                  15